United States Patent [19]

Stewart

[11] Patent Number: 5,799,331
[45] Date of Patent: Sep. 1, 1998

[54] HAND PROTECTOR

[76] Inventor: Gloria J. Stewart, 1331 W. Central Ave., No. 35, Santa Ana, Calif. 92704

[21] Appl. No.: 701,496

[22] Filed: Aug. 22, 1996

Related U.S. Application Data

[63] Continuation-in-part of Ser. No. 516,349, Aug. 18, 1995, abandoned.

[51] Int. Cl.$^6$ ................................................. A41D 19/00
[52] U.S. Cl. ........................................... 2/159; 2/158
[58] Field of Search ........................... 2/16, 21, 46, 50, 2/51, 59, 158–160, 161.6, 161.7, 907, 167, 168, 169

[56] References Cited

U.S. PATENT DOCUMENTS

| | | |
|---|---|---|
| 1,731,340 | 10/1929 | Lambert . |
| 2,847,676 | 8/1958 | Scott . |
| 2,864,090 | 12/1958 | Sutherland . |
| 2,976,540 | 3/1961 | Sutherland . |
| 3,409,010 | 11/1968 | Kron . |
| 4,677,697 | 7/1987 | Hayes . |
| 4,916,757 | 4/1990 | Berlin et al. . |
| 5,025,503 | 6/1991 | O'Brien ................... 2/169 |
| 5,127,127 | 7/1992 | Jarosinski . |
| 5,406,649 | 4/1995 | Bolembach . |

FOREIGN PATENT DOCUMENTS

| | | |
|---|---|---|
| 88-002550 | 5/1990 | Netherlands . |

*Primary Examiner*—Gloria M. Hale
*Attorney, Agent, or Firm*—Merchant, Gould, Smith, Edell, Welter, & Schmidt

[57] ABSTRACT

A low cost, disposable hand protector that provides a barrier between either hand and an item being handled comprises a thin contact sheet having overlying elements forming openings arrayed around a palm area for the fingers and for either thumb. The openings are formed by overlayer panels or webs which are themselves of thin sheet material. The topmost protector on a stack can be fitted on with a single insertion motion of the hand, and conforms to the hand while providing a barrier against contamination of an item being handled. The protector is released equally easily by a single motion.

15 Claims, 4 Drawing Sheets

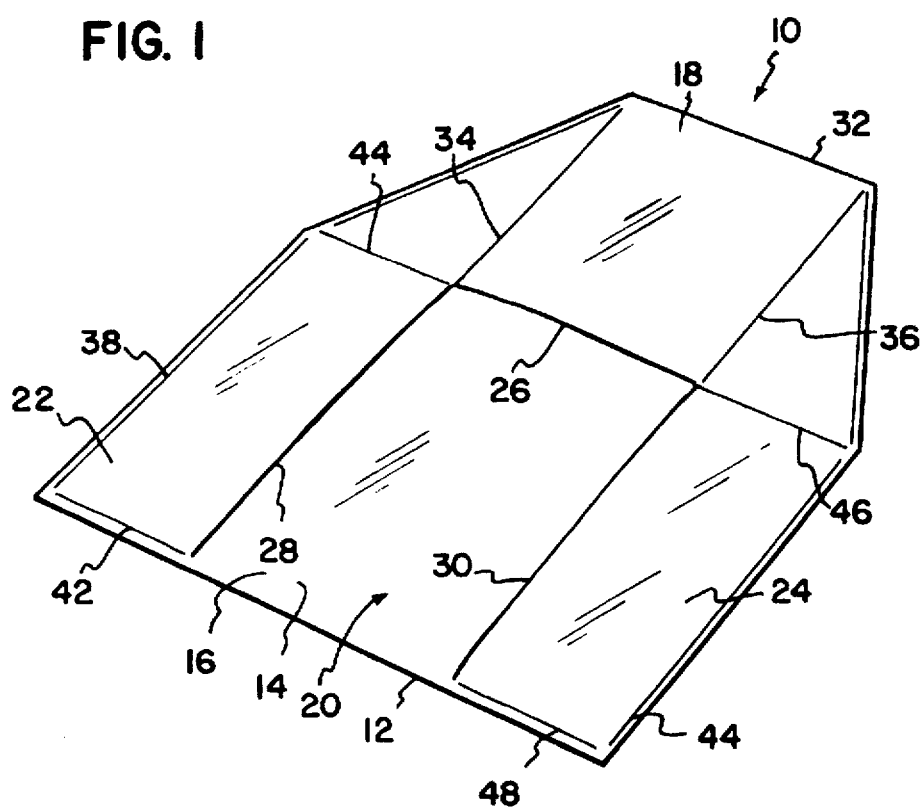

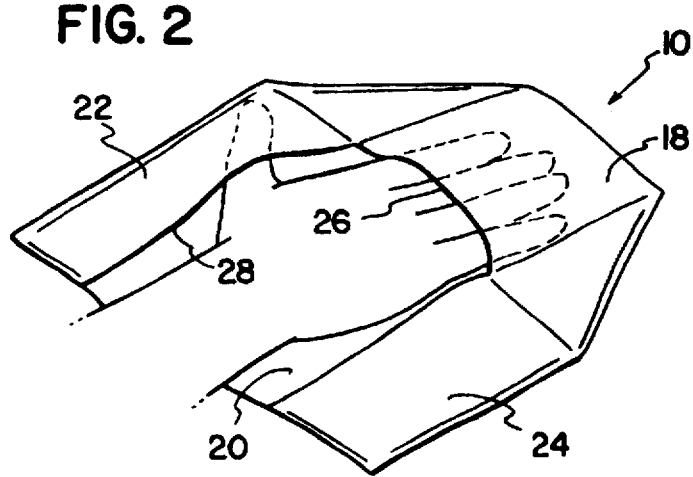
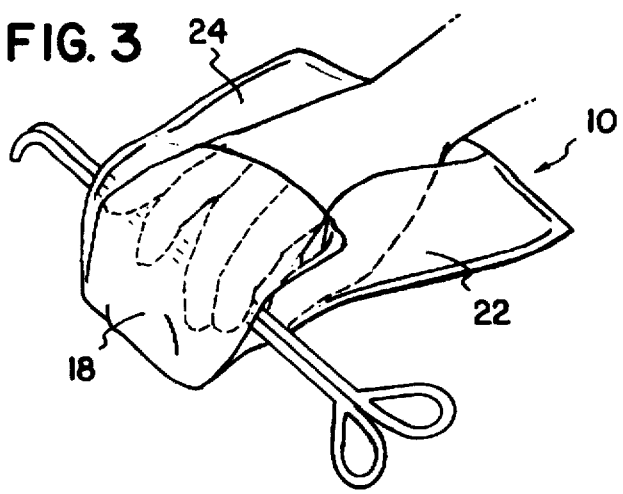

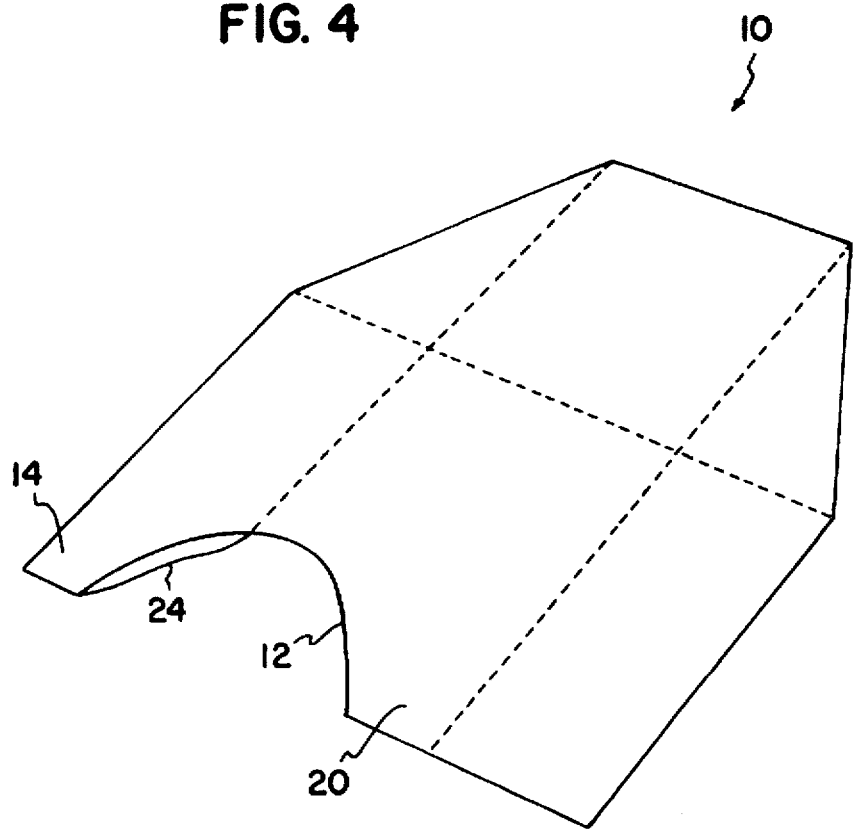

HAND PROTECTOR

RELATED APPLICATION

This application is a continuation-in-part of my previously filed application, Ser. No. 08/516,349, filed on Aug. 18, 1995 now abandoned.

BACKGROUND OF THE INVENTION

1. Field of the Invention

The present invention relates to a low cost handcovering or glove element, and more particularly to a disposable hand protector that is easily engaged on either hand, readily disposed of, and maintains a barrier between an item being handled and the person manipulating the item.

2. Description of Related Art

Numerous disposable mittens and gloves have been provided in the prior art to meet the growing demand for uncontaminated handling of foods, medical products and other items. They do not however, provide the desirable combination of low cost and disposability (single use) along with compatibility with either hand as well as quick and simple engagement and disengagement. Also, the hand-covering must secure against contamination whether in a completely sterile environment such as a surgical field, or in an environment such as a food-serving establishment in which customers insist on personalized protection against contamination, or in a laboratory where successive samples must be protected against cross contamination.

The hand-covering must also establish a barrier between the entire hand and the item, to secure against contamination. U.S. Pat. No. 3,409,010 discloses a disposable device that comprises a half glove or mitt formed so as to sheath only the knuckles of the human hand with a separate sheathing or fingerstall for the index finger but excluding the thumb.

Another disadvantage of many devices available is that they are not easily accessible but require tearing the glove free along perforated lines in order to use. Also, the existing gloves are not easily or quickly put on and taken off the user's hand but can require significant effort and manipulation of the glove by the other hand.

As another example, U.S. Pat. No. 4,677,697 issued to Hayes discloses a glove outline, preshaped into a hand format which is redundantly formed in two sheets of plastic where a perforation or cut line is pinched into the sheets allowing for separation. The disclosed glove contains a sealing structure at the wrist of the glove as well as a disinfectant or neutralizer bubble pack at the wrist end.

U.S. Pat. No. 4,916,757, yet a further example, discloses a glove formed of plastic films sealed together to form a contour providing a thumb, forefinger and a further receptacle to accommodate three fingers. The films are processed by bringing two films together and forming the contour seals and successive gloves are made separable at their adjacent interior seals by the provision of a line of perforations.

U.S. Pat. No. 5,406,649 discloses a disposable handcovering whereby a sheet of flexible, waterproof plastic material forms an enclosure with a cuff, to permit the hand to enter through the cuff into the enclosure. The cuff is adjustable to secure the enclosure about the wrist of the hand.

The objectives of ambidextrous capability, very low cost and easy use and disposition are not met by these or other known disposable gloves and hand coverings now in limited or widespread use.

SUMMARY OF THE INVENTION

In accordance with the invention, disposable hand protectors which can be slipped onto either hand comprise thin, pliant membrane or sheets having sufficient area to cover the entire face of the hand, and thin overlayer elements arranged about a palm protecting portion so that the fingers can be inserted into a central opening and either thumb can be inserted into one of two side openings. The positions are such that, although the digits fit in readily, the thumb and fingers are opposable and conform the sheet to the manipulating hand, enabling an item to be grasped through a complete barrier that extends across the palm as well as the fingers. In a particular example, the central finger opening is formed as a pocket accessible from a palm portion of the membrane, which is a thin plastic sheet. The thumb openings are on the opposite sides of the palm portion, so that the ingress openings define a U-shape outline. This device may be readily mass produced from a simple sheet by folding over the pocket forming layers and heat sealing to form the desired bonding lines. Another feature is that superimposed protectors form a level stack from which the top protector can be slipped on and removed by a single movement of the protected hand alone. Separation from the hand is by another unaided single-handed motion, so that protectors can be changed in a minimum of time.

BRIEF DESCRIPTION OF THE DRAWINGS

The figures in the drawing are briefly described as follows:

FIG. 1 is a somewhat diagrammatic perspective view of a hand protector in accordance with the invention;

FIG. 2 is a perspective view corresponding to FIG. 1 and showing the position of the hand inserted into the device;

FIG. 3 is another perspective view of the device of FIG. 1 showing how an item may be gripped through the protector;

FIG. 4 is a view of the back of the hand protector of FIGS. 1–3;

DETAILED DESCRIPTION OF THE INVENTION

Figure 5:
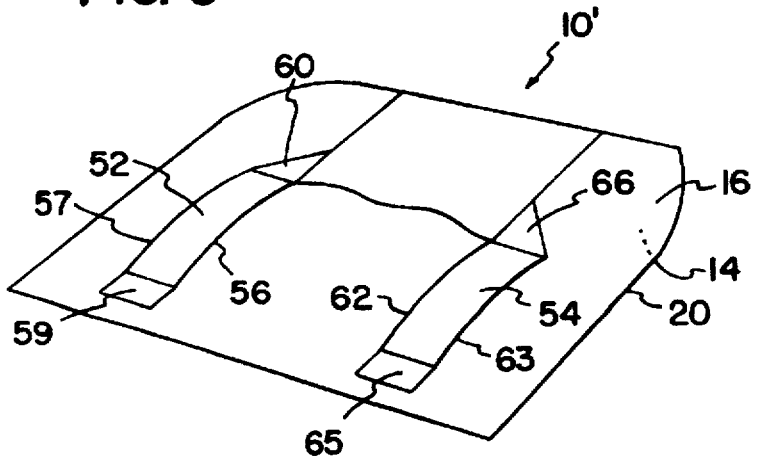
FIG. 5 is a view showing another example of a device in accordance with the present invention, wherein the side overlayer elements are formed as webs.

In the drawings, like reference characters indicate like parts throughout the several views. Referring initially to FIGS. 1 to 4, an example of a disposable hand covering element 10 is shown that is especially convenient to use and economic to manufacture. The disposable hand covering element 10 consists of a contact panel 12 of thin, pliant plastic material defining an item contact side 14 (FIG. 4) and a hand contact side 16 (FIGS. 1 and 2). The contact panel 12 includes a hand palm portion 20 or skirt, the hand palm portion 20 being large enough to be more than coextensive with the palm of a hand of average size.

A central overlayer element 18 is located adjacent to the hand contact side 16 of the contact panel 12. The central overlayer element 18 forms an open pocket with the contact panel 12, being separated from the contact panel 12 along a central edge 26 facing the hand palm portion 20 to form an opening for the fingers to be inserted. The span of the contact panel 12 between the sides of the central overlayer element 18 defines a flat surface large enough to accommodate at least a majority, typically all, of the fingers of a hand of average size. Also it is long enough to receive at least most of the length of the fingers. The central overlayer element 18 is joined to the contact panel 12 along a contact panel edge 32 adjacent to a central region of the contact panel 12 and along a left central edge 34 and a right central edge 36.

Adjacent to the central overlayer element 18 are side overlayer elements including a left overlayer element 22 and a right overlayer element 24. The central overlayer element 18, the left overlayer element 22 and the right overlayer element 24 are arrayed around the hand palm portion 20 such that the left overlayer element 22 and the right overlayer element 24 are at substantial angles with regard to the central overlayer element 18, and the ingress openings thus available define a general U-shape about the hand palm portion 20.

The left overlayer element 22 and the right overlayer element 24 each are large enough to accommodate respectively the thumb of a right hand or a thumb of a left hand. The left overlayer element 22 is separated from the contact panel 12 along a left open edge 28 to form an opening for a right hand thumb and is joined to the contact panel along a left edge line 38 and left edges 42, 44 extending from the left open edge 28. The right overlayer element 24 is separated from the contact panel 12 along an open edge 30 to form an ingress opening for a left hand thumb and is joined to the contact panel 12 along a right contact edge 40 and right edges 46, 48 extending from the right open edge 30.

The central overlayer element 18, the left overlayer element 22 and the right overlayer element 24 may be joined to the contact panel 12 by any appropriate means including but not limited to adhesives, stitching, or heat bonding. If adhesive is used, material may be conserved by using a line of spaced adhesive spots. Heatbonding or sealing will most often be used in a mass production forming process.

As best seen in FIG. 2 in this example, the contact panel 12 and the adjacent central overlayer element 18 form a pocket long enough to confine the fingers of an average hand past the middle knuckle. The central overlayer element 18 need not be a separate element from the contact panel 12 but may comprise a central extension of the contact panel 12 folded back at the contact panel edge and joined by conventional sealing means along the left central edge 34 and the right central edge 36 to the contact panel 12.

The contact panel 12 and the left overlayer element 22 form a left pocket and the contact panel 12 and the right overlayer element 24 form a right pocket, where each pocket is sufficiently large enough to confine the major part of the length of the thumb of the respective hand. The left overlayer element 22 and the right overlayer element 24 are also joined to the contact panel 12 respectively along the left edges 42, 44 and the right edges 46, 48 extending respectively from the left open edge 28 and the right open edge 30 to a left contact edge 38 and a right contact edge 40. The left overlayer element 22 and the right overlayer element 24 can be separate elements from the contact panel 12 or can be, as shown, side extensions of the contact panel 12 folded back at the left contact edge 38 and the right contact edge 40 and respectively joined along the left edges 42, 44 extending from the left open edge 28 and the right edges 46, 48 extending from the right open edge 30.

The central overlayer element 18, the left overlayer element 22 and the right overlayer element 24 are positioned in the approximate U-shape such that the left overlayer element 22 and the right overlayer element 24 are substantially opposite relative to each other, and sized so as to confine the inserted thumb such as to allow item manipulation between the thumb and fingers through the contact panel 12. FIG. 3 shows a typical manipulation of a medical instrument as it may be handed form an assistant to a surgeon. The central overlayer element 18, the left overlayer element 22 and the right overlayer element 24 confine the fingers and thumb in such ways that the pliant protector folds and conforms to the digital movements. The fingers and thumb compel the contact panel 12, including the hand palm portion 20 to move with and follow the bending of the fingers and hand, covering the palm at all times. To release the protector 10, the fingers and thumb are merely straightened out and if pointed downward, the protector will slip off by gravity or by wiping against the edge of a collector receptacle.

FIG. 5 is another example of a disposable hand covering element 10' in accordance with the invention. In this device the left overlayer element 52 and the right overlayer element 54 are smaller strips joined to the hand contact side 16 of the contact panel 12 and covering only part of a thumb. The elements 52, 54 are in the form of webs or bands for receiving the respective thumbs of a hand. The left overlayer element 52 is spaced from the contact panel 12 along its side edges 56, 57 and is joined to the contact panel 12 at its ends 59, 60. The right overlayer element 54 is spaced from the contact panel 12 along its side edges 62, 63 and is joined to the contact panel 12 at its ends 65, 66. The fingers of a user are inserted as in the example of FIGS. 1–4, but while the inserted thumb extends beyond the overlayer element 52 or 54, it nonetheless controls the folding and manipulation.

Figure 6:
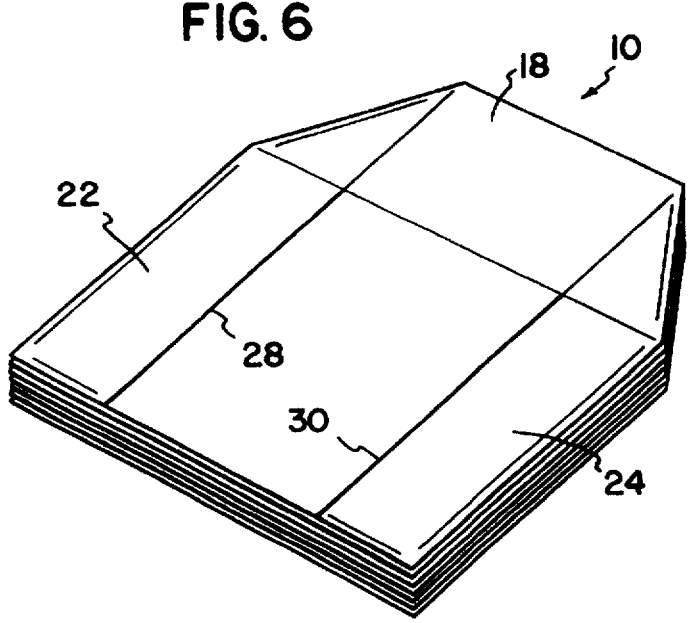
FIG. 6 is a view of a stack of the protectors ready for use.

FIG. 6 illustrates a feature of the present invention wherein several disposable hand covering elements 10 of uniform outlines are placed one upon the other forming a stack 70 of protectors with the hand contact side 16 of each uppermost. The openings formed by the central overlayer element 18, the left overlayer element 22 and the right overlayer element 24 do not disrupt, when stacked, a substantially flat level surface because the panels and overlayers are thin and planar. Thus, the fingers and the thumbs of either hand may be inserted into the openings of the top disposable protector 10 on the stack 70 for engagement and removal, in one motion, no matter how many are in the stack.

All examples of the disposable protector 10 feature this ease of fitting on one hand with no aid from the other hand, and also quick and unassisted removal by one hand alone. The disposable hand protectors also include ambidextrous capability, and can be manufactured at very low cost.

Although a number of forms and variations have been described, it will be appreciated that the invention is not limited thereto but includes all alternatives and expedients within the scope of the appended claims.

What is claimed is:

1. A dispensable, easily engaged and released glove for protected manipulation of items with either hand comprising:

(a) a contact panel of thin, pliant material having an item contact side and a hand contact side; and (b) a group of three thin, pliant, pocket forming elements on the hand contact side arrayed about a palm area and having ingress openings on the hand contact side adjacent to and open to the palm area, the pocket forming elements being positioned and sized to allow item manipulation of an item on the item contact side by thumb and fingers inserted into two of the pocket forming elements through the ingress openings.

2. A low cost, disposable hand-covering protector engageable by either a left or a right hand that shields an item to be handled from direct contact with the hand while allowing free manipulation of the item through the protector, comprising:

(a) a contact panel of thin, pliant material having an item contact side and a hand contact side having a hand palm portion; and (b) a group of thin pliant overlayer elements coupled to the contact panel on the hand contact side and defining ingress openings arrayed in a general U-shape about the hand palm portion for receiving a right thumb, a number of fingers as a group and a left thumb, the overlayer elements confining the inserted digits such that the protector conforms to digital movements of the thumb and the fingers whichever hand is used on the hand contact side.

3. The hand-covering protector of claim 2, wherein the overlayer elements comprise plastic membrane elements.

4. The hand-covering protector of claim 2, wherein the fingers overlayer element is in a central region adjacent to an edge of the contact panel opposite the palm portion.

5. The hand-covering protector of claim 2, wherein the overlayer elements for the thumbs comprise web members positioned adjacent opposite sides of the hand palm portion and joined at their ends to the contact panel on the hand contact side.

6. The hand-covering protector of claim 4, wherein the fingers overlayer element is a central extension of the contact panel folded back at the contact panel edge to form side edges and is joined along its side edges to the contact panel.

7. The hand-covering protector of claim 4, wherein the left thumb overlayer element and the right thumb overlayer element are side extensions of the contact panel along side edges of the contact panel adjacent end side of the hand palm portion and joined to the contact panel along edges of the contact panel spaced apart from the ingress openings.

8. The hand-covering protector of claim 1, wherein the hand protectors are of uniform outline and when stacked one upon the other with the hand contact side up the ingress openings lie in a substantially planar surface such that the fingers and thumbs of either hand may be inserted into the ingress openings of a top protector on the stack for engagement and removal of the protector from the stack.

9. A low cost, disposable glove engageable by either a left or a right hand that shields an item to be handled from direct contact with the hand while allowing free manipulation of the item through the protector, comprising:

(a) a contact panel of thin, pliant plastic having an item contact side and a hand contact side including a hand palm portion;

(b) a central overlayer element, coupled to the contact panel, and large enough to accommodate a number of fingers of a hand, the central overlayer element being separated from the contact panel along at least one edge adjacent the hand palm portion to form an opening for the fingers, and being long enough from the opening to enclose the majority of the fingers;

(c) side overlayer elements, comprising a left element and a right element, each being large enough to accommodate respectively the thumb of a right hand or a left hand, the side overlayer elements being separated from the contact panel along at least one edge adjacent the hand palm portion to form an opening for the respective thumb of the hand being used and the side overlayer elements can be manipulated through the protector; and (d) the central overlayer element and the side overlayer elements being arrayed about the hand palm portion of the contact panel in a general U-shape.

10. The glove of claim 9, wherein the overlayer elements comprise membrane elements of thin pliant plastic.

11. The glove of claim 10, wherein the central overlayer element and the side overlayer elements are bonded to the contact panel along the peripheral edges of the contact panel extending from the edge of the overlayer element that forms an opening for the respective fingers and thumb.

12. The glove of claim 10, wherein the side overlayer elements are on opposite sides of the central overlayer element, the edge opening of the central overlayer element being between the edge openings of the side overlayer elements.

13. A low cost, disposable hand-covering glove that shields an item to be handled from direct contact with the hand while allowing free manipulation of the item through the glove, comprising:

(a) a sheet of thin pliant plastic forming a contact panel defining a surface large enough to accommodate the span of a palm and fingers of a hand;

(b) said sheet being folded along a main fold line at one edge to form a top panel in face-to-face relation with the contact panel, the top panel having a length sufficient to encompass the fingers of a hand, said sheet further defining a skirt portion large enough to encompass the palm of a hand, and including line joinder means coupling the top panel to the contact panel to define a center finger pocket open in a first direction from the skirt portion; and (c) a pair of thumb pockets adjacent to the top panel and on opposite sides of the skirt portion, the thumb pockets being joined to the contact panel and open from the skirt portion in directions angled to the side of the skirt portion from the first direction and substantially opposite the skirt portion relative to each other.

14. The glove of claim 13, wherein the center finger pocket confines all the fingers other than the thumb and one of the thumb pockets confines the thumb of whichever hand is inserted such that the skirt portion covers the palm of the inserted hand and the contact panel glove conforms to movements of the inserted thumb and the fingers as they move in opposition to manipulate an item through the contact panel.

15. A low cost, disposable hand-covering element that shields an item to be handled from direct contact with the hand while allowing free manipulation of the hand, comprising:

(a) a contact panel of thin pliant plastic having an item contact side and a hand contact side;

(b) a top panel adjacent to the contact panel on the hand side and forming therewith a first pocket for fingers, and the first pocket being large enough to accommodate the span and at least the majority of the lengths of the fingers of a hand;

(c) two thumb pockets adjacent to the first pocket at substantial angles to said first pocket and on opposite sides of the hand contact side of the contact panel; and (d) a palm portion of the contact panel being disposed adjacent the fingers pocket and between the thumb pockets.

* * * * *